United States Patent [19]
Degouy et al.

[11] Patent Number: 5,257,528
[45] Date of Patent: Nov. 2, 1993

[54] DEVICE FOR STUDYING THE AGING OF A CIRCULATING FLUID UNDER SPECIFIC IMPOSED CONDITIONS

[75] Inventors: Didier Degouy, Houilles; José Brandely, Savigny s/Orge; Bernard Chatelain, Jouy Le Moutier; Pierre Gonzalez, Rueil-Malmaison, all of France

[73] Assignee: Institut Francais du Petrole, Rueil-Malmaison, France

[21] Appl. No.: 631,290

[22] Filed: Dec. 20, 1990

[30] Foreign Application Priority Data

Dec. 20, 1989 [FR] France .................. 89 17030

[51] Int. Cl.$^5$ .................. G01N 11/00
[52] U.S. Cl. .................. 73/53.01; 73/54.02; 73/64.56
[58] Field of Search .................. 73/153, 61.4, 64.1, 73/61 R, DIG. 8, 155, 53, 53.01, 54.02, 64.56, 54.01

[56] References Cited

U.S. PATENT DOCUMENTS

| | | | |
|---|---|---|---|
| 3,473,368 | 10/1969 | Roper | 73/64.1 |
| 4,483,189 | 11/1984 | Seol | 73/153 X |
| 4,501,143 | 2/1985 | Prior et al. | 73/53 X |
| 4,510,800 | 4/1985 | Prior | 73/153 |
| 4,510,801 | 4/1985 | Quigley et al. | 73/153 |

Primary Examiner—Hezron E. Williams
Assistant Examiner—Michael Brock
Attorney, Agent, or Firm—Antonelli, Terry, Stout & Kraus

[57] ABSTRACT

A device for studying an aging of a fluid circulated in a loop or closed circuit by imposing, for example, predetermined temperature, pressure or shear conditions on the fluid in order to determine rheologic properties of the fluid. The device includes a loading pump, a circulating pump, a filtration governor pump and an injection and draw-off pump, a flow meter, a viscosimeter for discontinuous measurings, a narrowing or reduction for causing a shearing of the fluid, a number of filters interconnected in series, a sampling cell, pressure and temperature pickups, heating jackets and heat insulation sheaths for maintaining a homogenous temperature all along the loop, and a control system which includes a programmable automaton associated with a microcomputer in order to pilot numerous operating sequences. The device is constructed so as to maintain constant conditions imposed on the fluid regardless of the type of measurements being effected.

11 Claims, 2 Drawing Sheets

DEVICE FOR STUDYING THE AGING OF A CIRCULATING FLUID UNDER SPECIFIC IMPOSED CONDITIONS

BACKGROUND OF THE INVENTION

The present invention relates to a device for studying, in an accelerated way, the aging of a circulating fluid under specific imposed conditions.

Two different types of studies can be rapidly carried out with the device according to the invention. It can be used for assessing the particular qualities of a fluid formula, within the framework of operations of qualification of this fluid for a particular use or for determining the constitutive equations of a certain fluid in time, when it is subjected to working conditions reproducing the extreme conditions encountered in operation.

The device according to the invention can notably be used for studying and testing muds such as those utilized during operations for boring wells such as oil wellbores.

During oil boring operations, a mud circulation under pressure is established between the surface installation and the zone surrounding the drill bit. The mud is utilized for cooling and lubricating the drill bit, as well as for cleaning the borehole by conveying the cuttings up to the surface. It is also used for creating a hydrostatic pressure sufficient to stabilize the walls of the well and to contain the fluids under pressure in the formations surrounding the wellbore. While going through the drilled zones, the mud is therefore subjected to considerable stresses depending on the characteristics of the wells, whether there are very high temperatures up to 200° C., high pressures of about several ten MPa or shearings at the level of the drill bit. The drilling conditions, the temperature and the nature of the formations frequently change. These changes may affect the properties of the drilling fluid. It is therefore important to make sure that the utilized fluid has the required properties and keeps them in time in spite of the stresses undergone.

The study of the behavior of drilling fluids can be carried out in the following manners.

Different measuring equipment can be included in the pumping plants delivering the fluid under pressure, in order to test, in a continuous manner, the characteristics of the fluid coming up from the drilling zone. Equipment for carrying out such tests is described, for example, in U.S. Pat. No. 4,635,735. The advantage of this type of measurings is that the studied fluid is subjected to the very conditions which prevail at the bottom of a wellbore. Nevertheless, its implementing requires the modifying and the adapting of an already existing installation for the circulation of a drilling fluid, which is not always possible.

The study of the behaviour of a fluid can also be performed in a laboratory. In an in situ installation, the measuring cycles are linked to the cycles of circulation of the drilling mud. The circulation rate being imposed and relatively slow, the study of the evolution of the fluid in time is generally very long. On the contrary, with laboratory equipment, the conditions prevailing in a drilling zone can be simulated concerning well-determined parameters by imposing a much faster circulation rate on the fluid. The fluid undergoes an accelerated aging thereby. Tests which would otherwise be very long are carried out rapidly. Besides, the possibility of varying at will certain experimental conditions reproducing the variations observed during the drillings allows multiple testings and measurings. Different equipment of this type are described in U.S. Pat. Nos. 4,483,189, 4,501,143 or 4,510,800.

The difficulty to be solved when a simulation equipment of this type is required consists in controlling the parameters acting on the studied fluid during each imposed working cycle well, by avoiding, at best, the uncontrolled parameter variations and, more generally, anything that might distort the measurements. Drilling fluids often contain corrosive (electrolytes) or abrasive (barium sulfate-clays) substances which, because of the testing conditions (temperature, circulation), are likely to attack the constituent materials of the circulation loops. The fluid can then be unintentionally contaminated by metallic ions which distort the measuring results. In the existing circulation loops, the heating of the fluid is most often performed in a single location. In order to take into account the limitations of certain equipment included in the loop, it is also compulsory to either cool the fluid or complicate the equipment. The experimental conditions achieved by the simulation loops do thereby not reflect at best the real conditions prevailing in the bottom of the wells.

It should also be noted that the equipment for studying circulating fluids become rapidly very complex if a complete set of measurings is desired. Maintaining during all the operations, on the fluid of the closed loop, precise experimental conditions such as temperature and pressure values become therefore very difficult to achieve.

SUMMARY OF THE INVENTION

The device according to the invention allows to achieve a set of measurings on a flow of fluid subjected to certain specific conditions such as those encountered during its use while circulating in a closed circuit, by avoiding the drawbacks cited above.

It is characterized by a combination of a loading pump for introducing into the closed circuit one or several fluids, a circulating diaphragm pump directly included in the closed circuit, in order to establish a flow of fluid in said circuit, control means for regulating the pressure difference between the outlet and the inlet of the circulating pump and on either side of the diaphragms thereof, a governor pump, an injection and draw-off pump, means for shearing the fluid circulating in the closed circuit, means for measuring the flow rates of the fluid in the closed circuit, means for measuring the rheologic characteristics of the fluid, measuring pickups, control valves, heating means adapted for heating the circulating fluid homogenously in all the parts of the device in contact with it, means for filtering the fluid, operated by the filtration pump, a supply set and a programmable control system connected with the measuring pickups and cooperating with the supply set to impose on the pumps and the control valves operating sequences for the achieving of the total measurings on the flow of fluid.

The heating means comprise, for example, a set of heating jackets the temperature of which is regulated.

The filtration means are, for example, included in a bypass circuit and comprise a plurality of filtration units with filtering sleeves interconnected in series, each one of them being linked by a valve to the filtration governor pump which selectively applies to said filtration units a differential pressure on either side of the filtering sleeves in order to divert fluid from the closed circuit.

Preferably, the circuit essentially comprises portions of circuit positioned in order to avoid the forming of deposits likely to locally limit the section of the closed circuit.

The programmable control system comprises, for example, a programmable automaton adapted for centralizing the values of the measured parameters, associated with a control microcomputer for imposing values on the regulation parameters and linking means for ensuring the interaction of the automaton and the control microcomputer, the device also comprising a visual display set showing at any moment the state of its different elements.

According to a preferred embodiment procedure, a pump with metallic diaphragms directly connected on the closed circuit is used as a circulating pump.

The control means comprise for example two pressure pickups respectively arranged at the inlet and at the outlet of the circulating pump and two pressure pickups arranged on either side of the diaphragms of this pump.

The device according to the invention allows to faithfully maintain the conditions imposed on a fluid for the following reasons.

The distribution of the heating means all along the closed loop allows an homogenous heating of all the fluid and avoids the occurrence of hot spots and cold spots which generate pressure regulation problems in the circuits, and, concerning hot spots, are likely to cause a local degradation of the circulating fluids.

Since the circulating pump can be directly connected on the closed circuit and therefore works following the pressures and temperatures imposed on the fluid, any deviation from the imposed conditions is avoided.

Moreover, with the programmable automaton used, which strictly imposes operating sequences on the different elements (valves, pumps, etc.) according to the measurements supplied by pickups and which controls their evolution, this automaton being under the direct control of an operator by a control microcomputer, complex sequences can be easily achieved without deviating from the imposed conditions, and the obtaining of representative results is facilitated thereby.

BRIEF DESCRIPTION OF THE DRAWINGS

Other features and advantages of the device according to the invention will be clear from reading the description hereafter of an embodiment procedure given by way of non limitative example, with reference to the accompanying drawings wherein.

DESCRIPTION OF THE PREFERRED EMBODIMENTS

Figure 1:
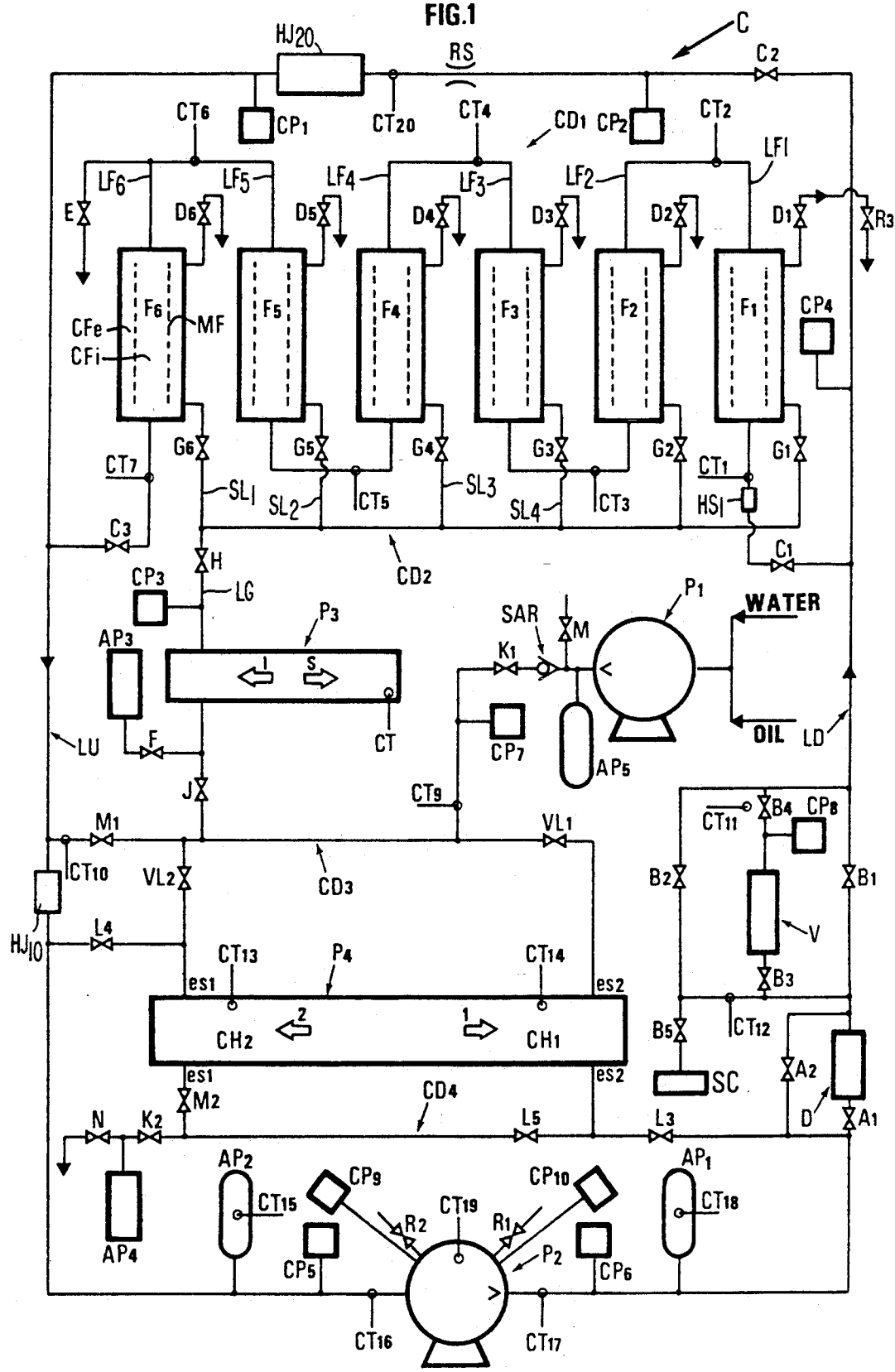
FIG. 1 diagrammatically shows the arrangement of the circuits of the closed loop.

The device diagrammatically shown in FIG. 1 comprises a closed circuit or loop C able to impose on a fluid circulating there precise conditions which reproduce those which it undergoes or has to undergo in operation. In the field of application of drilling muds, the device must impose on the fluid in the circuit certain parameters: temperature Tc, pressure Pc, shearing, etc, reproducing those encountered at the bottom of a well around the drill bit. The volume of circuit C is selected relatively low, about, for example, ten liters. It is made of an alloy able to withstand corrosion by saline solutions at high temperature and abrasion by solutions loaded with solid particles.

Loop C mainly consists of vertical-oriented circuit portions $LF_1$-$LF_6$ of circuits. It is optimized in this respect for reducing as much as possible the horizontal portions of connection circuit or those showing a slight horizontal inclination. Any possibly of sedimentation in circulation of the solid particles which the studied fluid may contain is eliminated thereby. It is thus possible to avoid restrictions of pipeline sections due to local accumulations of sediments and, at the same time, the uncontrolled shearing effects which they might cause to the circulating fluid. The reconditioning of the device at the end of the tests is also strongly simplified. The length of the loop is about ten meters for example.

Loop C is closed on a circulating pump $P_2$ that can work under a pressure of several ten MPa (50 MPa, for example), by allowing a differential pressure of about 10 MPa between its inlet (suction) and its outlet (discharge). A double-action pump with metallic diaphragms is preferably used, which directly acts on the circulating fluid without requiring a substantial change of temperature and pressure, and which allows to obtain a perfect tightness. This is possibly in view of the low volume of loop C because a slight liquid loss could cause a considerable pressure drop and, consequently, a fluid vaporization. A perfect tightness also guarantees that no loss compensation is necessary, and thus that it is the fluid that has been initially introduced in the loop which is studied throughout the test. The pump is especially designed for withstanding hot, abrasive and corrosive fluids. It causes no substantial cooling of the fluid. Two pulsation dampers $AP_1$ and $AP_2$ communicate with the circuit C near pump $P_2$. The first pulsation dampers $AP_1$ is arranged downstream from the pump, with the other pulsation damper $AP_2$ being located upstream. Their function consists in providing a constant flow rate in circuit C. Pump $P_2$ provides a flow rate of about 20 l/m, for example.

The flow rate is measured by a flowmeter D connected on the circuit by means of a valve A1. A bypass, controlled by a valve $A_2$ allows switching of the flowmeter D on or off, at will. On the circuit LD downstream from pump $P_2$, and downstream from the flowmeter D, a valve B1 is arranged and, in parallel with the valve $P_1$, a first circuit element comprising a viscosimeter V and two control valves B3 and B4, and a second circuit element controlled by a valve B2. A sampling circuit controlled by a valve B5 allows a connection a sampling cell SC of a well-known type. Fluid samplings operated at different moments of the aging cycle allow a following of the evolution of the physico-chemical properties of the fluid: pH, oxidation reduction potential, and to study the evolution of the structure of the clays and the degradation of the organic constituents. The measurings performed on the samplings can be usefully compared with the differents rheologic measurings achieved during the aging cycle. Viscosimeter V allows to carry out discontinuous measurings, at determined time intervals, for example, every hour.

Downstream from the flowmeter D, the downstream pipeline LD of circuit C is fitted with a section narrowing RS that can impose on the circulating fluid, at each cycle, a shear rate determined according to a given application. In the case of a drilling fluid, a narrowing which applies a shear rate of about $10^4$ s$^{-1}$ with the same order of magnitude as the shear rate undergone by the fluid flowing through a drill bit is selected. The access to the narrowing is controlled by a valve $C_2$. Two pressure pickups $CP_1$, $CP_2$ are arranged on the circuit C on either side of the narrowing RS in order to measure the pressure drop caused by the narrowing RS.

Because of the low capacity of the circuit and of the flow rate of circulating pump $P_2$, the fluid rapidly flows through loop C. It is therefore possible to multiply the frequency of the flows through narrowing RS and quicken the aging of the studied fluid.

A filtration cell is arranged in a bypass line on narrowing RS and control valve $C_2$. This filtration cell comprises for example six filtration units $F_1$ to $F_6$ interconnected in series by circuit portions $LF_1$–$LF_6$ on a common bypass $CD_1$ the access to which is controlled by a valve C1.

This structure of filters $F_1$–$F_6$ in series is advantageous. The chambers of the respective filters $F_1$–$F_6$ and of the valves $G_1$–$G_6$ and $D_1$–$D_6$ can be tooled in a single block, which avoids using numerous valve bodies and connections and, in a general way, the number of valves necessary for controlling the filtration structure is less than for another configuration.

Each filtration unit $F_1$–$F_6$ comprises a cavity separated into two coaxial chambers CFi and CFe by a filtering sleeve MF. When the pressure is the same in the two chambers, the filtration unit is inactive. The fluid flows through the filter while remaining in the center of filtering sleeve MF. In order to set up a differential filtration pressure in the filtration units and thereby force the fluid to flow through the filtering sleeves MF, each peripheral chamber CFe is linked by a line portions $SL_1$–$SL_6$, respectively and control valve $G_1, G_2 \ldots G_6$, to a common pipeline $CD_2$, which itself is linked by another line portion LG and a valve H to a filtration governor pump $P_3$ adapted for creating and maintaining a pressure difference $\Delta P$ constant between the pressure P in the closed circuit C and a pressure P' prevailing in the annular chambers CFe of the different filtration units $F_1$ to $F_6$, during the total filtration process when any one of them is made active. The filtration units are fitted with drain circuits controlled by drain valves $D_1, D_2 \ldots D_6$. A drain valve E is connected with the outlets of filters $F_5$ and $F_6$. The filtration governor pump $P_3$ is, for example, piston or of the plunger type pump.

The running of this pump $P_3$ is controlled by comparing the values measured by a pressure pickup $CP_3$ connected with circuit element $CD_2$ downstream from valve H and a pressure pickup $CP_4$ connected with circuit C. A pulsation dampener $AP_3$ is connected with pump $P_3$ by a control valve F. It allows the discharge of pump $P_3$ when the latter is full. A control valve J makes pump $P_3$ communicate with a circuit element $CP_3$ linked by a valve Ml to pipeline LU of the main circuit C upstream from circulating pump $P_2$, and by two control valves L1 and L2 respectively with two inlets-outlets es1, es2 of a double-action piston pump $P_4$ allowing the injection and the draw-off. The valve $VL_4$ makes inlet es1 communicate with the upstream circuit LU. The functions of pump $P_4$ are to compress the fluid in order to bring the fluid to the operating pressure; to regulate, by draw-off or injection, the pressure of the fluid in the circuit during the test; to balance the pressure of the fluid during the tests, notably during the filtration and sampling phases; to inject into the circulating fluid suspended solid particles characteristic of a ground, for example, or saline solutions representing formation fluids; and to carry out fluid sampling out of the circuit.

The two inlets-outlets es1, es2 of pump $P_4$ are respectively connected by valves $M_1$ and $L_5$ with a portion of the circuit $CD_4$ which communicates by a control valve K2 with a pulsation dampener $AP_4$. The injection inlet-outlet es2 of pump $P_4$ communicates through a valve $L_3$ with the downstream circuit LD of the main circuit C on the outlet side of circulating pump $P_2$. The valve $L_4$ controls the communication between inlet-outlet es1 and the upstream pipeline LU of the main ciricuit C on the inlet side of circulating pump $P_2$.

The loading of the main circuit with fluid is achieved by a loading pump $P_1$ the outlet of which communicates with a pulsation dampener $AP_5$ and, by a flap valve SAR and of a control valve $K_1$, with the circuit element $CD_3$.

Two pressure pickups CP5 and CP6 are directly arranged upstream and downstream from pump P2. Comparing the indications shown by these two pickups allows to check whether the pressure drops all along circuit C are compatible with the maximum differential pressure allowable by circulating pump $P_2$. A pressure pickup $CP_7$ is connected on circuit element $CD_3$ and its measurings allow the automatic control of loading pump $P_1$. If the pressure that it measures is lower than a set low threshold, the loading pump $P_1$ loads pump $P_1$. If it is higher than a high threshold, loading pump $P_1$ stops. A pressure pickup $CP_8$ is arranged in the circuit of the viscosimeter V in order to measure the pressure in the latter, notably during the measuring phases where it is isolated from the rest of the circuit. Two pickups $CP_9$ and $CP_{10}$ are utilized for measuring the pressures on either side of each metallic diaphragm of circulating pump $P_2$. Their measurements are used for automatically controlling the pressures on either side of each diaphragm. It is thereby possible to avoid excessive working conditions in case of an anomaly.

Two drain valves $R_1$-$R_2$ are arranged in circulating pump $P_2$. They are utilized during the fluid loading phases.

The operating pressure is partly obtained by warming up the fluid. All the circuits and the constituent elements in contact with the circulating fluid (pumps, filtration cell, pulsation dampeners, viscosimeter, etc) are fitted with an insulating sheathing. The equipment comprises a considerable number of, for example, about thirty heating jackets HJ, ... $HJ_N$ distributed all along main circuit C and the bypass circuits, with each one of heating jackets being fitted with a temperature pickup and having its own temperature regulation of the P.I.D. type (Proportional band, Integral time, Derivative time). These heating jackets provide a homogenous heating of the total loop and allow to bring the fluid all along the circuits up to a temperature that can reach 200° C. This is important because, during the static phases, there must be neither hot spots nor cold spots. In fact, because of the bad pressure transmission in thixotrope fluids, the presence of hot spots in the circuits would cause a local rise in pressure beyond the safety limits bringing about a breakdown and also a possible local degradation of the fluid. The existance of cold spots could decrease the pressure of the fluid below a set low threshold and also cause a breakdown.

Numerous temperature and pressure pickups respectively referenced $CT_1, CT_2 \ldots CT_{20}$ and $CP_1, CP_2 \ldots CP_{10}$ are arranged in various points of the main circuit C and of the bypass circuits, in order to measure the temperatures of the circulating fluid.

Figure 2:
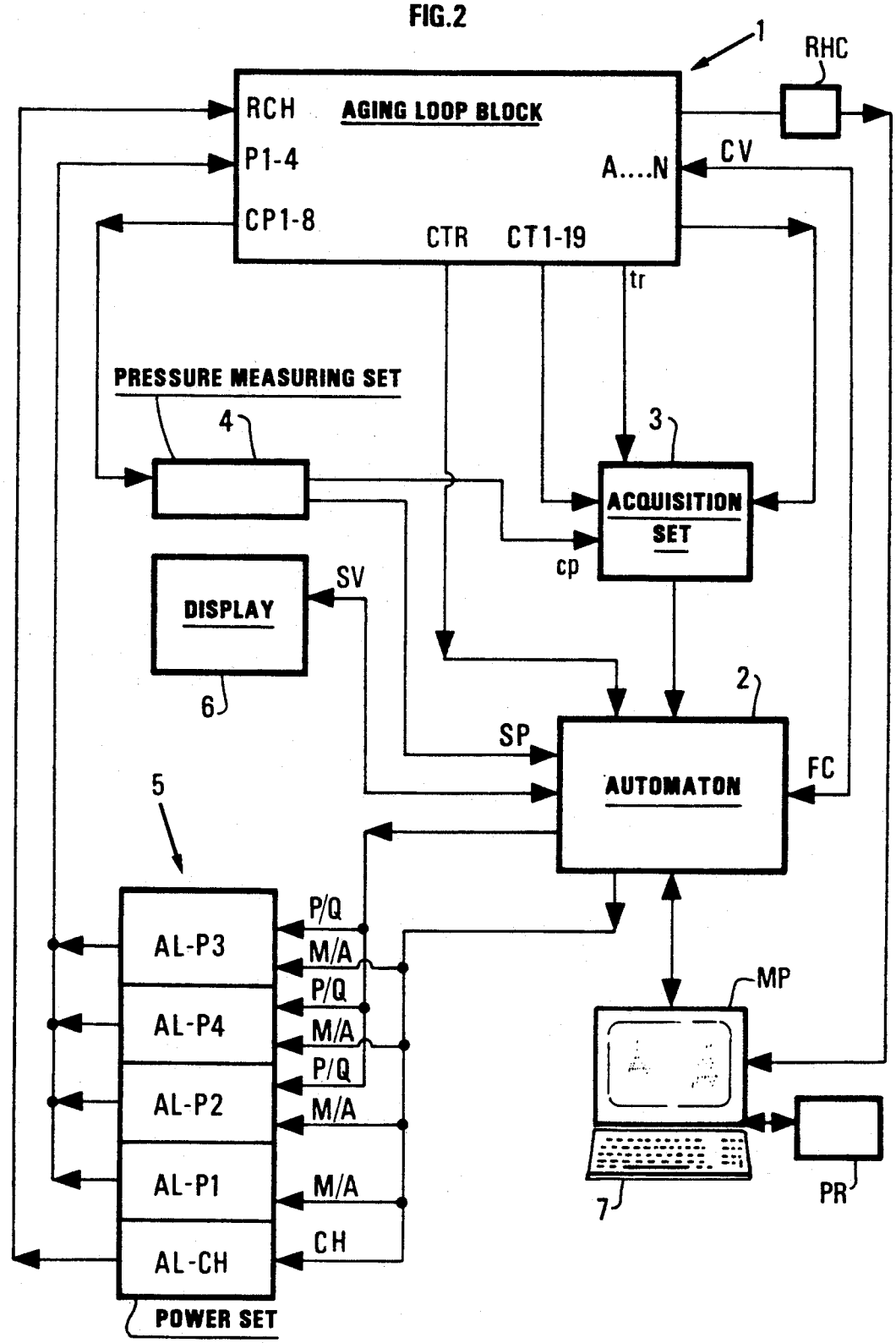
FIG. 2 is a schematic view of the control and check elements acting on the circuits of the closed loop.

In FIG. 2, block 1 represents the total circuits and elements of FIG. 1. A programmable automaton 2 of a well-known type, such as an M.G PB400 automaton (non limitative example), is used for managing all the processes occurring in the block 1. It is associated with a control microcomputer MP. Automaton 2 is coupled with an acquisition set 3 adapted for multiplexing, sampling and digitizing the different temperature and pressure signals measured in block 1. Acquisition set 3 directly receives the analog signals delivered by flowmeter D and temperature pickups $CT_1$ to $CT_{20}$, as well as the signals TR delivered by the temperature pickups respectively associated with the heating jackets.

The pressure signals of pickups $CP_1$ to $CP_{10}$ are applied to a pressure measuring set 4 which delivers the values cp of the measured pressures to the acquisition set 3.

Automaton 2 receives the measurements digitized by the acquisition set 3 and different working signals CTR. These are signals coming from block 1: on/off position signals of pumps $P_1$ to $P_4$, end of travel signals FC received from the different pumps $P_1$ to $P_4$ and from valves A to N, signals showing the speed of rotation of circulating pump $P_2$. There are also signals coming from pulse emitters (not shown) associated with pumps $P_3$ and $P_4$ which generate pulses indicating the exact position of their respective pistons and which allow to control their respective injection rates (Q) when their flow is regulated.

In response to the measurements and signals it receives and to the instructions imposed by microcomputer MP, automaton 2 elaborates orders. Those concerning the valves are directly sent into block 1.

According to the working phases and sequences that will be explained more fully hereinbelow, the pumps can be regulated as for their flow rate (Q) or their pressure (P). Other orders are applied to a power set 5 comprising five units. Four units $ALP_1$, $ALP_2$, $ALP_3$ and $ALP_4$ receive from automaton 2 on/off signals for the pumps $P_1$ to $P_4$ of block 1 on one hand and set values for pumps $P_2$ to $P_4$ depending on whether their pressure or their flow rate is to be regulated. In response to these four signals, these $ALP_1$, $ALP_2$, $ALP_3$ and $ALP_4$ units respectively provide to the pumps the currents that are necessary for operating them. A fifth unit AL-CH controls the supply relays of the heating jackets in block 1, in response to an appropriate instruction coming from automaton 2 and elaborated from values read from the PID regulation parameters.

The device also comprises a visual display unit 6 where all the circuits, pumps, valves and pickups are shown in a synoptic way, and which shows at any time the state of its different constituent elements. The synoptic display unit 6 receives from automaton 2 the appropriate display signals SV. A printer PR is associated with microcomputer MP.

The phases (automatic mode) and the sequences (semiautomatic mode) start from the synoptic display unit 6 through the display on the latter of a serial and validation number of the corresponding operation. When a phase is over in the automatic mode, automaton 2 repositions the loop in the aging phase and waits for an order to start another, more specific one.

The automaton is programmed for automatically managing the different working phases of the circuits of block 1, as will be described more fully hereinbelow.

Nevertheless, the operator can intervene in the development of the processes in progress by control microcomputer MP linked to automaton 2. Microcomputer MP receives the measurements transmitted by the automaton and, in return, transmits set values to it. It also directly receives the measurements coming from viscosimeter V by an interface set RHC. The values imposed by microcomputer MP are adapted to viscosimeter V by this interface set RHC.

Different working processes of loop C included in block 1 are described hereafter in order to show the operating sequences which are led by automaton 2.

The different working phases of the device according to the invention will be achieved by modifying its conformation, by changing the state of the pumps and of the valves.

Filling the Loop with Clear Fluid (Phase 01)

The piston of pump $P_4$ is arranged in a median position and that of pump $P_3$ in an stopped position.

The operation of filling with clear fluid will be carried out by pump $P_1$ in several sequences in order to limit air trappings at the maximum (sequences 01 to 04).

Testing the Loop at the Set Pressure Pc and at Room Temperature (Phase 02)

The loop is first tested at the discharge pressure of pump 1 in order to detect any possible sizeable leakages (sequence 1). The set pressure is then obtained by injecting basic fluid into the main circuit by pump $P_4$. The injection will be alternately performed through the two chambers of the pump:

Injection in direction 1 (sequence 02)
Injection in direction 2 (sequence 03)

These sequences will be managed by automaton 2, the sequence changing being determined by an indicator of the travel end of the piston.

The injection through one of the chambers will cause a pressure decrease, measured by pickup $CP_7$, in the other chamber. The loading of the latter is automatically performed with pump P1. Too high a stress of the pump is avoided by operating it or by stopping it according to the measured pressure p7.

After checking the tightness at the set pressure, the loop is depressurized (sequence 04) and the piston of pump P4 is brought into a stop position in direction 1.

Filling the Loop with Drilling Fluid

This operation is achieved in several phases each one comprising several sequences in order to obtain the best possible scavenging of the clear fluid.

Filling the Injection/Draw-Off Pump ($P_4$): Phase 03

The piston of the pump is displaced into direction 2 with the simultaneous filling of chamber 1 by pump $P_1$ (sequence 01), then the operation is repeated in the other direction (sequence 02). Sequences 01 and 02 are doubled.

Filling the Rest of the Loop (Phase 04)

It is performed in several stages or sequences:
filling of the lower part of the loop (sequence 01)
filling of the bypasses of flowmeter D and of viscosimeter V and of the first five filters $F_1$ to $F_5$ (sequence 02)
filling of the flowmeter D of the downstream pipeline for the opening of valve B1 and of the first five filters $F_1$ to $F_5$ (sequence 03)

filling of the pipeline through the opening of $C_2$ and of the sixth filter $F_6$ (sequence 04)

filling of the pipeline going back towards pump $P_2$ and of the sixth filter $F_6$ (sequence 05).

It should nevertheless be noted that the filling with drilling fluid does not concern circuit $CD_2$ that is linked to the annular chambers of the filtering sleeves MF, which only contains clear fluid.

Filling the Viscosimeter (Phase 05)

This operation is performed only when the fluid contained in the loop has the required characteristics, indicating thereby a total displacement of the initial fluid. After reducing the flow rate of pump $P_1$, viscosimeter V is filled (sequence 01) and then isolated by closing valve $B_3$ and the loop is tested at a testing pressure (sequence 02).

Setting the Temperature and Pressure Conditions

Circulation Beginning (Phase 06)

The circulating pump is started in order to homogenize the temperature of the fluid in the loop during this phase of setting into condition (sequence 01). The circulation takes place at a low rate because, at this point, the pulse dampers can only partly fulfill their flow regulating function.

Heating and Regulation Phase (Phases 07 and 08)

During the heating phase, pump $P_4$ is stopped as long as one of the instructions (Pc or Tc) has not been approached.

Two situations can be encountered:
Pc reached before Tc (phase 07)
Tc reached before Pc (phase 08)

If $P=Pc$ $T<Tc$ (phase 07), fluid has then to be drawn off in the loop by pump $P_4$ in order to be able to go on heating without exceeding the set pressure (sequences 01 and 02 according to the direction of running of the pump).

If $T=Tc$ $P<Pc$ (phase 08), fluid must then be injected into the loop by pump $P_4$ in order to reach the set pressure Pc (sequences 01 and 02 according to the direction of running of the pump).

During this phase, the pressure in the second chamber should not fall under a threshold value set in order to avoid a fluid vaporization. Appropriate on-off instructions are therefore transmitted by automaton 2 to pump $P_1$ according to the measured pressure $P_7$.

Phases 7 and 8 being totally managed by automaton 2, they can be advantageously integrated to phase 6 as subsequences of the process of temperature and pressure conditions setting. As soon as this process is over, passing to the next phase 09 is automatic.

Testing Phases

Aging in Circulation (Phase 09)

The circulation flow rate is progressively brought up to the selected value after reaching instructions Pc and Tc (sequence 01). In the following operations of these testing phases, the position of the valves ($L_1$ to $L_5$ and $M_2$) depends on the direction of running of pump $P_4$ and on the regulation phase in progress (injection or drawoff). They can, for example, have the conformation of sequences 01 and 02 of phase 7 during the drawoff, or the conformation of sequences 01 and 02 of phase 08 during the injection.

Measuring the Rheologic Properties (Phase 10)

This is achieved after exchanging the fluid within viscosimeter V and isolating the latter. The filling of viscosimeter V comprises several stages:
reduction of the flow rate in the main circuit
expelling the old fluid in the pipelines giving access to the viscosimeter by circulating it for a given time (sequence 01)
expelling the old fluid contained in the viscosimeter (sequence 02)
isolation of the viscosimeter and increase in the flow rate in the main circuit (sequence 03).

The measuring phase can begin at the closing of valve $B_4$.

By the control keyboard 7, the operator selects the parameters conditioning the rheologic measurings:
maximum shear rate, shear upgrade, shear step and downgrade for the rheologic curves;
shear rate and shear time for the thixotropy measurings;
gel time for the "standardized" gel measurings.

Then the operation selects the type of measuring to be carried out on a menu and starts it.

At the end of the measuring cycle decided by the operator, an automatic stopping of the rotating of the rotor of viscosimeter V and the resumption of the conformation of sequence 01 of phase 09 with the opening of valve $B_4$ take place.

Dynamic Filtration Measurings (Phase 11)

The process comprises:
isolation of narrowing RS and circulation through filters $F_1$ to $F_6$ (sequence 01),
setting up of the differential filtration pressure $\Delta P$ in pump $P_3$ (sequence 02),
a filtration sequence through the selective opening of valve $G_1$ to $G_6$ of the selected filter and of valve which marks the starting moment of the filtration measuring. The differential pressure is maintained by displacing in direction S the piston of pump 3 (sequence 03). The volume of the filtrate is measured during a determined time interval or until the volume of the filtrate reaches a limit that has also been determined.

The following items are recorded during this measuring phase according to time: the filtered volume, the circulation flow rate, the differential filtration pressure and the temperature of the fluid near the selected filter, canceling the differential pressure $\Delta P$ through compression of the fluid by governor pump $P_4$ (sequence 04).

The filtration phase ends with the opening of valves $G_1$ to $G_6$ and the resumption of the aging process in the main circuit (phase 09 sequence 01).

Static Filtration Measurings (Phase 12)

To achieve this phase:
the section narrowing RS is insulated and the circulation is diverted through filters $F_1$ to $F_6$ (sequence 01) in order to change the fluid at rest,
the circulation is restored in the main circuit and a differential filtration pressure $\Delta P$ is set up in pump $P_3$ (sequence 02), and
valve $G_1$ to $G_6$ of the selected filter is selectively opened (sequence 03).

It is operated in the same way as for the dynamic filtration (phase 11, sequence 03), except that, during this phase, the circulation flow rate is not recorded. The phase of static filtration ends with the cancellation of the differential pressure ΔP (sequence 04), by opening the valve G concerned, and by resuming the aging conformation in the main circuit (phase 09, sequence 01).

Purging the Filtration Governor Pump (P₃) (Phase 13)

This operation may appear necessary before starting a filtration phase. The pump is first of all isolated (sequence 01) and then partly emptied by displacing the piston (sequence 02). In this sequence, pump $P_3$ is set in the flow rate priority mode. The remaining fluid is then compressed, after the closing of valve F, until the pressure is restored (sequence 01), then valve H and the concerned valve G are opened. The aging conformation is then resumed (phase 09, sequence 01).

Fluid Contamination Operations

Injection of a Contaminating Fluid (Phase 14)

During this phase, pump $P_4$ works in the flow rate priority mode and will therefore not fulfil its pressure regulation part in the testing loop. This function will be fulfilled by pump $P_3$ with the filters already utilized. During this phase, the following stages are successively performed:
- displacing the piston of pump $P_4$ into a stop position in direction 1 with the transfer of the fluid from chamber 1 towards chamber 2 (sequence 01),
- filling chamber $CH_1$ by displacing the piston in direction 2 with the simultaneous purging of chamber $CH_2$ (sequence 02),
- repeating sequences 01 and 02 to check the quality of the contaminating fluid, before the injecting of the contaminating fluid at the required flow rate (sequence 03).

Phase 14 is preceded by a purging of pump $P_1$ and of a part of the piping by means of a hand-operated valve M located between pump $P_1$ and check valve SAR.

Purging the Contaminating Fluid at the End of the Injection (Phase 15)

After purging pump $P_1$ and part of the circuit and replacing the contaminating fluid by drilling fluid, the rest of the circuit is purged by pump $P_4$. Chamber 1 is therefore filled by the pump $P_1$, by the displacement of the piston in direction 2 (sequence 01). The fluid to be removed is then transferred from chamber $CH_1$ towards chamber $CH_2$ (sequence 02) and then purged through the filling of chamber $CH_1$ with drilling fluid (sequence 03).

Sequences 02 and 03 are repeated to make sure that the contaminated fluid has been correctly replaced. The aging conformation is then restored (phase 09, sequence 01).

Flowmeter

The flowmeter is intermittently integrated in the circuit when the acquisitions of the flow rate measurings are necessary. Consequently, from phase 05 onward, the positioning of valves $A_1$, $A_2$ is conditioned by the cycle of acquisition of the flow rate measurings, at regular intervals, the modification of the conditions on the flow rate during the operation of loading of the viscosimeter, for example, and the phase in progress (for example, continuous acquisition during the operations of dynamic filtration).

The control software of automaton 2 and of microcomputer MP allow a complete managing of the installation. The device performs a complete piloting of the successive phases and sequences from instructions imposed by the operator by means of the microcomputer:
- it manages the processing of the filtration data and of the rheologic measurements and their presentation in the form of curves or tables and, at defined intervals, it produces systematic statements of the operations achieved;
- it adjusts all the PID regulators of the temperature regulation means.

Besides, it is also adapted for detecting faulty operations and for locating them, which allows to correct them much more rapidly.

We claim:

1. A device for obtaining a set of individual measurements of a flow of fluid circulating in a closed circuit and subjected to conditions similar to conditions encountered during utilization, the device comprising a loading pump for introducing into the closed circuit at least one fluid, a circulating pump including diaphragms directly incorporated in the closed circuit to set up a flow of fluid in said closed circuit, automatic control means for regulating a pressure difference between an outlet and an inlet of the circulating pump and on either side of the diaphragms of the circulating pump, a filtration governor pump, an injection and draw-off pump, means for shearing the fluid circulating in the closed circuit, means for measuring flow rates of the fluid in the closed circuit, means for measuring rheologic characteristics of the fluid, measuring pickups, control valves, heating means adapted for heating the circulating fluid homogeneously in all the parts of the device in contact with the heating means, filtration means for filtering the fluid, a governor pump for operating the filtration means, a power supply set and a programmable control system connected with the measuring pickups and cooperating with the power supply set to impose operating sequences on the pumps and the control valves for obtaining control of said set of individual measurements on the flow of fluid.

2. A device as claimed in claim 1, wherein the heating means comprise a set of heating jackets, and wherein means are provided for regulating a temperature of the heating jackets.

3. A device as claimed in claim 1, wherein the filtration means are included in a bypass circuit and comprise a plurality of filtration units fitted with filtering sleeves interconnected in series, each of said filtration units are linked by a valve to the filtration governor pump which is adapted to selectively apply to said filtration units a differential pressure on either side of the filtering sleeves to divert the fluid out of the closed circuit.

4. A device as claimed in claim 1, wherein the diaphragms of the circulating pump are metallic diaphragms.

5. A device as claimed in claim 1, wherein the automatic control means comprise two pressure pickups respectively arranged near the inlet and the outlet of the circulating pump and two pressure pickups arranged on either side of the diaphragms of the circulating pump.

6. A device as claimed in claim 1, wherein the filtration governor pump and the injection and draw-off pump are piston pumps.

7. A device as claimed in claim 1, wherein the closed circuit and all metallic parts in contact with the fluid are fashioned of an alloy adapted to withstand corrosion by saline solutions at high temperatures and abrasion by solutions loaded with solid particles.

8. A device as claimed in claim 1, wherein the closed circuit includes circuit portions positioned in such a manner so as to avoid a forming of deposits in sections of the closed circuit.

9. A device as claimed in claim 1, further comprising a cell for sampling fluid under imposed predetermined conditions.

10. A device for obtaining a set of individual measurements of a flow of fluid circulating in a closed circuit and subjected to conditions similar to conditions encountered during utilization, the device comprising a loading pump for introducing at least one fluid into the closed circuit, a circulating pump fitted with diaphragms directly incorporated in the closed circuit to set up a flow of fluid in said closed circuit, automatic control means for regulating a pressure difference between an outlet and an inlet of the circulating pump and on either side of the diaphragms of the circulating pump, a filtration governor pump, an injection and draw-off pump, means for shearing the fluid circulating in the closed circuit, means for measuring flow rates of the fluid in the closed circuit, means for measuring rheologic characteristics of the fluid, measuring pickups, control valves, heating means adapted for heating the circulating fluid homogeneously in all parts of the device in contact with the heating means, filtration means included in a bypass circuit and comprising a plurality of filtration units fitted with filtering sleeves interconnected in series, each filtration unit being linked by a valve to the filtration governor pump which is adapted to selectively apply a differential pressure to said filtration units on either side of the filtering sleeves so as to divert the fluid out of the closed circuit, an electric supply set and a programmable control system connected with the measuring pickups and cooperating with the electric supply set for imposing operating sequences on the pumps and the control valves for obtaining control of said set of individual measurements on the flow of fluid.

11. A device as claimed in any one of claims 1 to 10, wherein the programmable control system comprises a programmable automaton adapted to centralize values of measured parameters, associated with a control microcomputer for imposing values on regulation parameters, and linking means for providing an interaction of the automaton and the control microcomputer, and wherein a visual display unit is provided for displaying at any moment a state of different components of the device.

* * * * *